United States Patent [19]

Bryan et al.

[11] Patent Number: 5,046,028
[45] Date of Patent: Sep. 3, 1991

[54] SYSTEM FOR CALIBRATING, MONITORING AND REPORTING THE STATUS OF A PH SENSOR

[76] Inventors: Avron I. Bryan, 26 Country Club Rd., Cocoa Beach, Fla. 32931; Michael R. Cushman, 521 Brandonwood Rd., Kingsport, Tenn. 37662

[21] Appl. No.: 624,961

[22] Filed: Dec. 10, 1990

Related U.S. Application Data

[63] Continuation-in-part of Ser. No. 306,064, Feb. 6, 1989, Pat. No. 5,016,201.

[51] Int. Cl.5 .................... G06F 15/46; G01N 27/26
[52] U.S. Cl. ............................ 364/550; 204/153.21; 204/401; 204/412; 204/435; 364/496; 364/571.01
[58] Field of Search ...... 364/550, 496, 571.01–571.08, 364/551.01, 500; 204/401, 412, 416, 418, 435, 153.21; 324/438, 439; 73/1 R, 1 H

[56] References Cited

U.S. PATENT DOCUMENTS

| | | | |
|---|---|---|---|
| 4,109,505 | 8/1978 | Clark et al. | 23/1 R |
| 4,285,792 | 8/1981 | McGandy | 324/438 |
| 4,288,308 | 9/1981 | Hach | 324/438 |
| 4,447,775 | 5/1984 | Breuker et al. | 324/438 |
| 4,650,562 | 3/1987 | Harman, III et al. | 324/438 |
| 4,686,011 | 8/1987 | Jäckle | 324/438 |
| 4,713,618 | 12/1981 | Carlson et al. | 73/1 R |
| 4,777,444 | 10/1988 | Beijk et al. | 324/438 |
| 4,800,513 | 1/1989 | Deutsch | 364/550 |
| 4,961,163 | 10/1990 | Bryan et al. | 364/496 |

Primary Examiner—Kevin J. Teska
Attorney, Agent, or Firm—Macdonald J. Wiggins

[57] ABSTRACT

A device for use in a system for providing on-line, real-time monitoring of the condition of a sensor immersed in a process solution, the sensor having a membrane, by periodically generating known changes in characteristics of the process solution adjacent the membrane, the device providing a fixed volume of the process solution adjacent the membrane, the fixed volume being independent of a flow rate of the process solution. The device include a shield of non-conductive material, and having a retracted position permitting flow of the process solution past membrane, and an extended position enclosing the membrane to provide a fixed, stationary volume of process solution adjacent said membrane. The shield is selectively moved from its retracted position to its extended position during monitoring of the condition of the sensor.

13 Claims, 1 Drawing Sheet

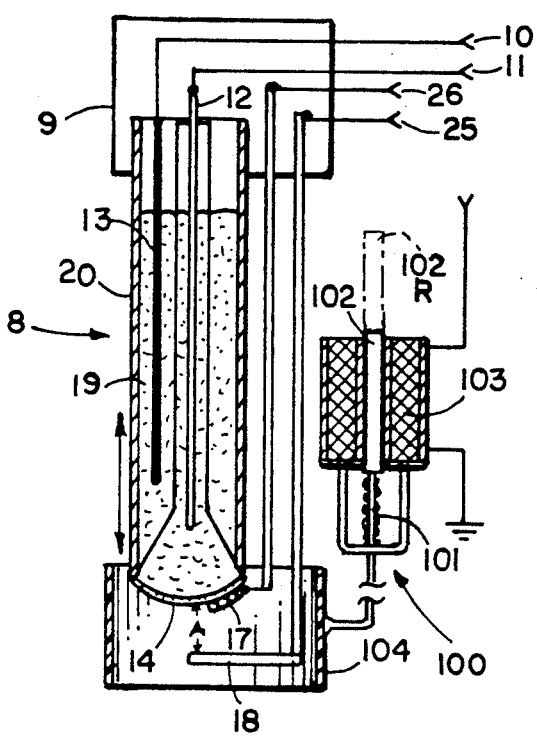
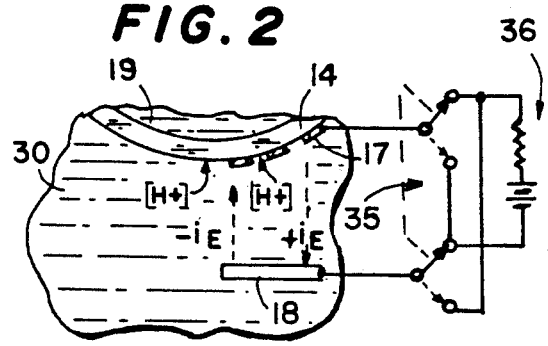
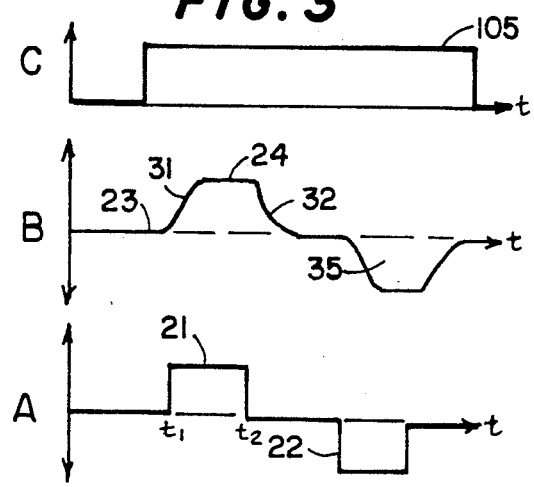
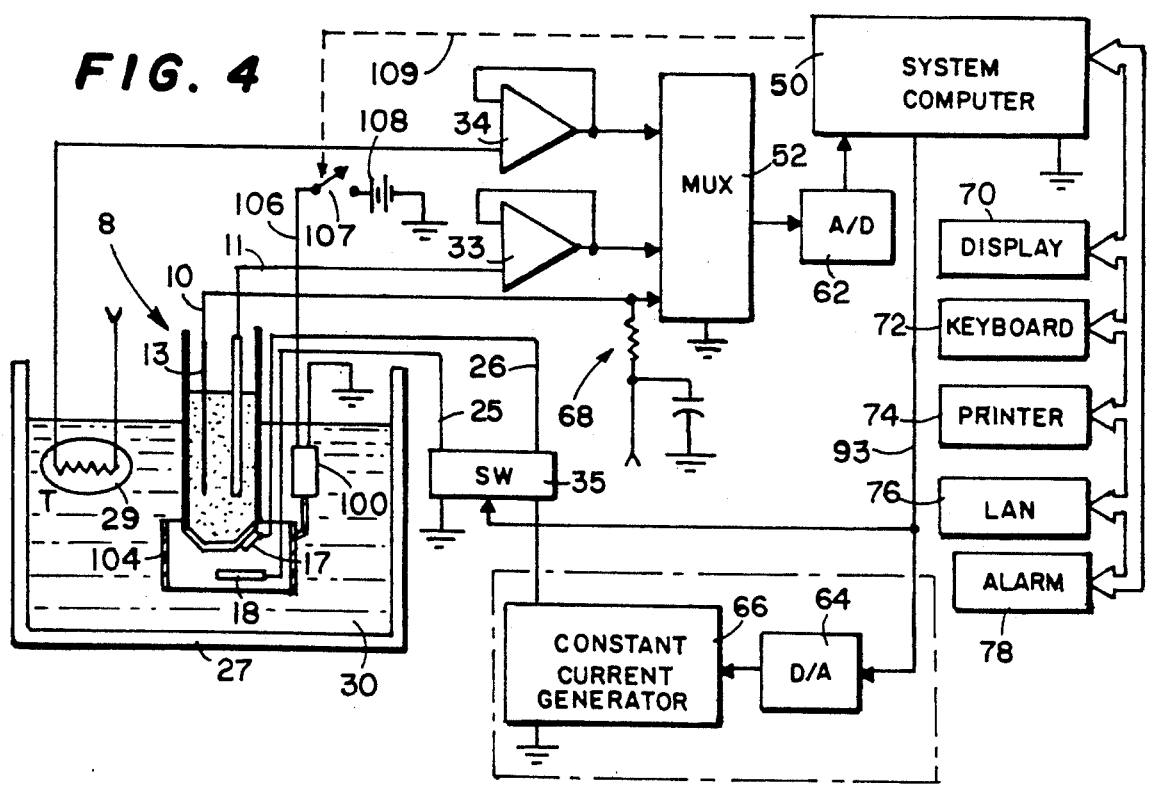

SYSTEM FOR CALIBRATING, MONITORING AND REPORTING THE STATUS OF A PH SENSOR

This application is a continuation-in-part of copending patent application, Ser. No. 07/306,064, filed Feb. 6, 1989, now U.S. Pat. No. 5,016,201.

FIELD OF THE INVENTION

The present invention relates to a pH calibrating and monitoring system operating in a process solution containing water, and more particularly to an improvement in a system for monitoring of the operational condition of a pH sensor of the system.

DESCRIPTION OF THE PRIOR ART

The pH of processes containing water is important in many industrial processes and is critical for processes based on microorganisms; for example, fermentation, recombinant DNA processes, and waste water treatment. The present real time measurement of pH in industrial processes normally utilizes the glass pH electrode. The pH signal developed by the sensor is in response to the concentration of hydrogen ions in the solution. Specifically, the glass electrode is immersed in the process solution and the difference in hydrogen ion concentration on the inside and outside of the pH sensitive glass membrane generates a potential proportional to the process hydrogen ion concentration. The operation of the sensor is maintained at a state in which the signal from the sensor is proportional to the hydrogen ion concentration in the sample.

There are a number of problems that can occur with this measurement system. For example, the glass membrane can become coated by the process or can change due to structural failure, such as cracks, leakage or degradation. In the sensor body, the physical condition of the electrodes and the condition of the electrolyte directly affect the sensor signal. These problems can occur in prior art systems without being detected resulting in false readings. Such failures can produce significant losses in time and money.

U.S. Pat. No. 4,961,163, owned by the present applicants, discloses one approach to this problem. The present invention represents improvements to the invention disclosed therein.

There is a need for a pH sensor system in which calibration of the sensor can be performed, and in which defects in the pH sensor can be detected in real time while a process is on-line, and for assuring the accuracy of such procedures independently of process solution flow rates thereby, reducing the probability of undetected failures. Operating costs would thus be significantly reduced.

SUMMARY OF THE INVENTION

The present invention is a pH measurement system having a unique real time, on-line capability for continuously monitoring the pH sensor of the system, and for periodically calibrating and testing the sensor and the system response by generating, in the process solution, a short temporary controlled change in the hydrogen ion concentration at the external surface of the sensor. The system utilizes the change in hydrogen ion concentration to periodically calibrate the total system and to test the sensor response to the controlled changes.

A novel pH sensor is provided having two electrodes external to the sensor membrane. A first of the two electrodes is mounted directly on the surface of the pH sensor glass membrane and is in the form of a conductive open grid. The second electrode is located adjacent the first electrode at a distance of one fourth inch or more therefrom. When the system is in use, the pH sensor and the two additional external electrodes are disposed in the process solution or stream that may vary in the flow rate of the solution past the pH sensor. The two external electrodes are connected to a current source by a polarity reversing switch so each can function interchangeably as an anode or a cathode. A small controlled direct current from the source is periodically passed from anode to cathode through the solution for a short controlled period of time.

The current produces an electrolytic action in the aqueous solution. The major electrochemical reaction is electrolysis of water. By having the second electrode attached directly to the surface of the sensor membrane, the electrolysis and the resulting pH change are confined to a static layer of the solution directly at the membrane-layer interface. This layer defines a fixed volume, permitting the ability to step to a predetermined pH level.

When the current direction causes the electrode at the surface of the membrane to act as a cathode, a base is produced. When the membrane electrode acts as an anode, an acid is produced. The amount of pH change at the surface of the membrane can thus be produced in a predetermined amount and calibration of the system can be effected.

The calibration and measurement monitoring system is controlled by a computer with appropriate algorithms and additional control hardware to perform all of the functions of pH measurement, testing and analysis of the sensor and system response. To this end, the signal from the pH sensor is applied to an analog-to-digital (A/D) converter and the digitized signals are input to the computer. The computer processes the signals and converts the results to operate numerical read-outs of the pH being measured. A controlled change in pH at the sensor is produced by driving the external electrodes with a dc pulse. The computer analyzes the amplitude, rise time and decay time of the resulting change in the sensor output signal and compares these values with stored normal values. Thus, the operational status of the system may be determined.

The computer is programmed to periodically generate a short signal to calibrate or to test the sensor system. A computer controlled generator provides a direct current between the two external electrodes by applying a low level dc potential between the two external calibration and test electrodes. The polarity of the potential is periodically reversed, thus producing sequential pulses of base and acid at the sensor. The acid or base produced by the test pulses at the membrane produces a detectable change in pH over the process solution average pH which is monitored in the normal manner. During the test period of the measurement system, the system pH delivered to users and control systems is maintained at the last average reading before the application of the test signal. The effects of the artificially generated pH change on the sensor are monitored and compared with past behavior stored in the system memory for system check purposes; such data are not reported as changes in pH in the solution process.

The system computer, having issued the test signal, thereafter monitors the pH signal deviation from the normal pH level in the process solution. System computer algorithms then compare the amplitude response, initial speed of response, and decay response to the short applied signals to monitor both sensor and system performance. If the sensor response comparison is outside of selectable limits, an automatic on-line recalibration routine is exercised to determine if the sensor has failed or degraded. If the calibration procedure is successful, all parameters are updated in the computer, and the recalibration reported. If recalibration is not successful, alarms are produced.

During the test period, as discussed hereinabove, changes are caused to occur above and below the average pH of the process. However, when the flow rate of the process solution varies with time, such changes will affect the the amplitudes of the test pulses of negative and positive ions from test to test. To avoid such effects from varying flow rates, a movable shield surrounding the sensor is provided.

The shield is of a nonconductive material, and is normally positioned well above the sensor membrane and the two external electrodes. When a test is to be conducted, a solenoid or other means, moves the the shield to surround the membrane and the external electrodes, thereby enclosing a repeatable small volume of the process solution. The test pulses are then produced, and analyzed as previously described. After analysis, the shield is retracted to its normal position. As will now be recognized, the tests will be independent of the flow rate of the process solution.

It is preferred to include a temperature sensor in the process on-line near the pH sensor. The output of the temperature sensor is converted to digital form which is used by the system computer to thereby compensate the pH sensor concentration readings.

It is therefore a principal object of the invention to provide a pH measurement system having real time, on-line means for periodic testing of a pH sensor, recalibration of the system if changes in the sensor are detected, and for providing a static, fixed volume of process solution during testing and recalibration.

It is another object of the invention to provide a pH measurement system for aqueous process solutions by periodically producing a controlled increase and a controlled decrease in pH of a shielded volume of solution to permit comparisons of the dynamic characteristics of such changes with normal system characteristics.

It is still another object of the invention to provide a shield for surrounding a stable volume of process solution only during testing and recalibration of a pH sensor in situ.

These, and other objects and advantages of the invention, will be apparent from the following detailed description when read in conjunction with the drawings.

BRIEF DESCRIPTION OF THE DRAWINGS

FIG. 1 is a cross sectional view of a pH sensor with external test and monitoring electrodes, and a process flow shield, for use in a pH measuring system in accordance with the invention;

FIG. 2 is a partial view of the sensor and electrodes of FIG. 1 illustrating generation of pulses of increased and decreased pH for test purposes;

FIG. 3 shows the flow shield control pulse, and the current and pH waveforms produced by the circuit of FIG. 2, and FIG. 4 is a schematic and block diagram of a preferred embodiment of the system of the invention utilizing a computer for operating the flow shield, and for measuring and testing of the sensor of the invention having external electrodes.

DETAILED DESCRIPTION OF THE PREFERRED EMBODIMENT

The invention is a pH monitoring system including means for calibration and for monitoring of pH in an aqueous process solution. A novel pH sensor 8, shown in cross section in FIG. 1, has two external electrodes 17, 18 to provide means for calibrating, testing, analyzing, and reporting the pH sensor status as well as the total system response. A standard pH sensor 8 is mounted to a bracket 9 from which external electrode 18 depends. A second external metallic electrode 17 is attached to, or deposited on, the external surface of sensor membrane 14 and covers a relatively small area of the membrane surface.

The reference electrode 13 of sensor 8 is preferably silver and is immersed in a saturated silver chloride electrolyte 19. The sensor electrode 12 is preferably formed from silver. Electrodes 13 and 12 are disposed in a housing 20 having an open lower end. The sensor membrane 14 is formed from pH sensitive glass covering the end of housing 20. External test electrode 17 is attached to membrane 14. Electrode 17 functions as a cathode or anode, and is formed as a grid so as not to interfere with normal ion diffusion to glass membrane 14. Test electrode 18 also functions either as an anode or cathode, and is spaced a distance A from test electrode 17. Distance A is not critical but is normally more than 0.25 inches. Test electrodes 17 and 18 can be of any suitable material; preferably, platinum. As will be noted, reference electrode 13 of sensor 8 is connected to lead 10, and sensor electrode 12 connects to lead 11. Electrode 17 is connected to lead 26, and electrode 18 connects to lead 25.

A process flow shield 104 is attached to an armature 102 of solenoid 100, and is shown in its operated position. Solenoid winding 103 is energized via lead 106 from a voltage source $+V$, causing armature 102 to move from a retracted position 102R to the operated position as shown by armature 102, thereby compressing spring 101. When power is removed from winding 103, shield 104 is retracted as indicated by arrow B to expose electrodes 18 and 17, and membrane 14 to normal process solution flow.

Turning now to FIG. 2, a portion of sensor 8 is shown immersed in process solution 30. Membrane 14 is indicated with hydrogen ions [H+] incident thereon. The measurement system will normally measure the concentration of such hydrogen ions in solution 30.

The condition of the electrodes 12, 13 of FIG. 1, electrolyte 19 and membrane 14 are monitored by periodically producing controlled changes in hydrogen ion concentration directly at the sensor membrane 14. A direct current source 36 and 3-position switch means 35 are connected across electrodes 17 and 18. Switch 36 is in the center OFF position during normal operation of the pH measurement system. Controlled changes in pH are produced by electrolysis from a direct current, either $+i_E$ or $-i_E$, between electrodes 17 and 18, when switch is in positions S1 or S2. With switch in position S2, the current direction is such that electrode 17 at the surface of sensor membrane 14 is negative relative to electrode 18. In solution 30, the reaction at the membrane surface produces one molecule of hydrogen and two negative hydroxide ions. Thus, the solution, at the membrane, becomes more basic. With the switch in position S1 as shown, electrode 17 is positive. The reaction produces an oxygen molecule and four positive hydrogen ions. The solution at the sensor now becomes more acidic. These changes in pH are in agreement with either the Bronsted theory of acidity (acid=source of protons; base=acceptor of protons) or the Lewis theory of acidity (acid=electron pair acceptor, base=electron pair donor). See Reference 1, pp 496-9.

Referring to FIG. 3, a positive current pulse 21 ($+i_E$) from anode 18 to cathode 17 is produced in a short interval $t_1-t_2$ as shown on line A. The electrolysis of water solution 30 produces an increase in negative hydroxide ions resulting in an increase in the normal pH reading 23 on line B to a maximum level 24. The dynamics of the electrolysis produce a specific rise time 31 and decay time 32 of the increase. Similarly, when the current pulse direction reverses, pulse 22 produces positive hydrogen ions resulting in a pulse 35 of reduced pH.

Prior to the application of pulses 21 and 22 in line A, voltage +V (105) is applied to solenoid 100 as indicated on line C, causing shield 104 to be moved to the position of FIG. 1. Thus, electrodes 17 and 18 are shielded during production of test pulses 21 and 22. After decay of pulse 35, line B, the voltage +V is removed from solenoid 100, and shield 104 is retracted to permit process flow past membrane 14.

When the controlled changes in the measured value of pH from sensor 8 occur, each change is analyzed for amplitude 24, rise time 31, and decay time 32. The characteristics of these waveforms at calibration are stored and subsequent measurements are compared to the calibration. Any physical changes in sensor 8 will affect the sensor's response to the test pulse. An automatic recalibration procedure is generated by the control computer if a change is out of preselected limits. If the recalibration is successful, normal pH monitoring is continued; if not, an alarm may be generated.

The preferred implementation of the invention is shown by the schematic and block diagram of FIG. 4. A process solution 30 for which the oxygen concentration is to be measured is shown in a tank 27. A pH sensor 8 is shown immersed in the solution 30. In addition, a temperature sensor 29, which may be of any electrical type, is provided to allow automatic temperature compensation of the pH sensor response.

A system computer 50 is provided having a number of stored programs. For monitoring the condition of sensor 8, pulses of increased and decreased pH are periodically generated at electrode 17 on membrane 14 as discussed above. A stored program in the system computer 50 commands a constant current generator 66 via D/A converter 64 to generate the electrolysis current pulses on a programmable periodic basis. Computer 50 controls switch 35, which may be an electronic switch, to change the polarities of electrodes 17 and 18, and closes switch 107 as indicated by dashed line 109 to operate shield 104. Further, the current amplitude and time duration of the current pulses are programmable to accommodate the process solution characteristic. The current to generate the changes in hydrogen ion concentration is applied via leads 25, 26 and via polarity switch 35 to the electrolysis electrode 17 and 18.

Having described the test procedure controlled by computer 50, the operation of the system will now be discussed. The sensor electrode 12 dc output is available via lead 11 to an emitter follower circuit 33 which drives the multiplexer (MUX) 52. Temperature sensor 29 provides a voltage signal proportional to temperature via emitter follower 34 to MUX 52. The potential on the reference voltage line on reference electrode lead 10 is connected directly to MUX 52. Bias is provided by network 68. Multiplexer 52 has its output connected via an analog-to-digital (A/D) converter 62 to system computer 50.

System computer 50 includes stored programs to perform statistical analyses of the data contained in the dc signal from electrode 12. The programs analyze the response of the sensor to pulses 21 and 22 of FIG. 3, and measure the solution pH. Thresholds for the normal operating parameters of the sensor 8 are programmable and are entered into system computer 50. Whenever any of the programmed thresholds is exceeded, recalibration is automatically attempted. A failure alarm is actuated if the recalibration cannot be accomplished. The process solution pH, the sensor response times, calibration parameters, and the process temperature are available for real time monitoring on the system display 70, printer 74; a local area network 76; and alarm 78.

Initial calibration of the system may be carried out by entering appropriate keyboard commands via keyboard 72 or via the local area network 76. The system computer program may select new threshold values for the sensor 8 and system test and monitoring signals based on the calibration.

Although specific illustrations of the preferred embodiment have been presented, these are for exemplary purposes only and various alternative arrangements may be used without departing from the spirit and scope of the invention. In addition, the periodic perturbation of pH in the region of the sensor is applicable to any type of pH sensor, for instance fiber optic based pH probes.

REFERENCE

1. Donald I. Hamm, "Fundamental Concepts of Chemistry", Appleton-Century-Crofts, New York, N.Y., 1969.

We claim:

1. In a real time, on-line calibration, test and monitoring system for measurement of pH having a pH sensor immersed in a process solution, the pH measuring system having a permeable membrane, the improvement comprising:
   a) a first electrolysis electrode disposed in the process solution adjacent said permeable membrane;
   b) a second electrolysis electrode immersed in said process solution and spaced apart from said first electrode;
   c) a source of direct current for selective connection to said first and second electrodes;
   d) control means for periodically connecting and controlling said direct current source to cause said direct current to flow through said solution between said first electrode and said second electrode for producing electrolysis in said process solution to thereby produce temporary changes in the concentration of hydrogen ions incident on said sensor, said changes in hydrogen ions producing temporary changes in pH relative to the pH due to the process, each of said changes characterized by a rise time, a maximum amplitude, and a decay time;
   e) means for comparing said rise times, magnitudes, and decay times of said changes with calibrated values and for detecting deviations from calibrated values indicative of a change in characteristics of said pH sensor;

f) a movable shield having an extended position surrounding said membrane of said sensor, and said first and second electrolysis electrodes during flow of said current, and a retracted position exposing said membrane to a flow of said process solution; and g) means for moving said shield between said extended position and said retracted position.

2. The improvement as defined in claim 1 in which said shield is formed of non-conductive material.

3. The improvement as recited in claim 1 in which said shield moving means is a solenoid having an armature attached to said shield.

4. The improvement as recited in claim 3 in which said control means is a switch connected between said current source, and said first and second electrodes, and said computer includes means for periodically operating said switch to sequentially move said switch from an open position to a first closed position to produce a first current between said electrodes in a first direction, and to move said switch to a second closed position to produce a second current in a second direction, and operating said solenoid to move said shield to said extended position when said switch is in its closed positions.

5. The improvement as recited in claim 1 which said comparing and detecting means includes a system computer.

6. The improvement as recited in claim 5 in which said system computer includes a program for measuring and storing calibrated values of said rise times, said magnitudes, and said decay times and for comparing monitored ones of said increases and decreases in pH with said calibrated values and for displaying deviations from such calibrated values.

7. The improvement as recited in claim 6 in which said program includes thresholds for said calibrated values and means for performing an automatic recalibration of said system when a threshold is exceeded.

8. The improvement as recited in claim 7 in which said program includes means for enabling alarms when said recalibration is not successful.

9. A device for use in a system for providing on-line, real-time monitoring of the condition of a sensor immersed in a process solution, the sensor having a permeable glass membrane, by periodically generating known changes in characteristics of the process solution adjacent the membrane, the device providing a fixed volume of the process solution adjacent the membrane, the fixed volume being independent of a flow rate of the process solution, comprising:

a shield of non-conductive material, said shield having a retracted position permitting flow of the process solution past said membrane, and an extended position enclosing said membrane to provide a fixed, stationary volume of process solution adjacent said membrane; and means for selectively moving said shield between said retracted position and said extended position.

10. The device as defined in claim 9 in which said moving means includes;

a solenoid;

an armature movable within said solenoid, said armature attached to said shield; and means for maintaining said armature in said retracted position when said solenoid is not energized.

11. The device as defined in claim 10 which further includes control and timing means for periodically energizing said solenoid for extending said shield, and for denergizing said solenoid for returning said shield to said retracted position.

12. The system as recited in claim 10 in which said control and timing means is a computer, said computer programmed to provide control and timing of operation of said solenoid.

13. The system as defined in claim 12 which includes an electronic switch, and said computer includes means for periodically operating said switch.

* * * * *